United States Patent [19] [11] 4,041,948
Flam et al. [45] Aug. 16, 1977

[54] DIGITAL TAMPON
[75] Inventors: Eric Flam, East Brunswick; Doris Phyliss Partyka, Milltown, both of N.J.
[73] Assignee: Johnson & Johnson, New Brunswick, N.J.
[21] Appl. No.: 708,507
[22] Filed: July 26, 1976
[51] Int. Cl.² .......................... A61F 13/20
[52] U.S. Cl. ....................... 128/285; 128/270
[58] Field of Search .............. 128/270, 285, 262, 263
[56] References Cited
U.S. PATENT DOCUMENTS

| 2,328,795 | 9/1943 | Finks | 128/270 X |
| 2,676,594 | 4/1954 | Milcent | 128/285 |
| 3,298,369 | 1/1967 | Pirie | 128/285 |
| 3,340,874 | 9/1967 | Burgeni | 128/285 |
| 3,358,686 | 12/1967 | Asaka | 128/270 X |
| 3,865,108 | 2/1975 | Hartop | 128/270 X |
| 3,971,378 | 7/1976 | Krantz | 128/285 |
| 3,986,511 | 10/1976 | Olofsson et al. | 128/285 |
| Re. 28,674 | 1/1976 | Guyette | 128/285 |

FOREIGN PATENT DOCUMENTS 348,707   2/1905   France .................. 128/270

Primary Examiner—Aldrich F. Medbery
Attorney, Agent, or Firm—Jason Lipow

[57] ABSTRACT

A digital tampon is provided which is sufficiently rigid to allow for digital insertion but which subsequently, during use, loses its rigidity to provide comfort when worn and when removed. The tampon comprises a rigidifying element extending longitudinally and disposed centrally with respect to the axis of the tampon. The element is chosen to have a dry resistance to compression sufficiently high enough to allow insertion and a wet resistance to compression, less than the dry resistance, and sufficiently low enough to allow the tampon to expand when wet and be comfortable in use and during removal.

8 Claims, 9 Drawing Figures

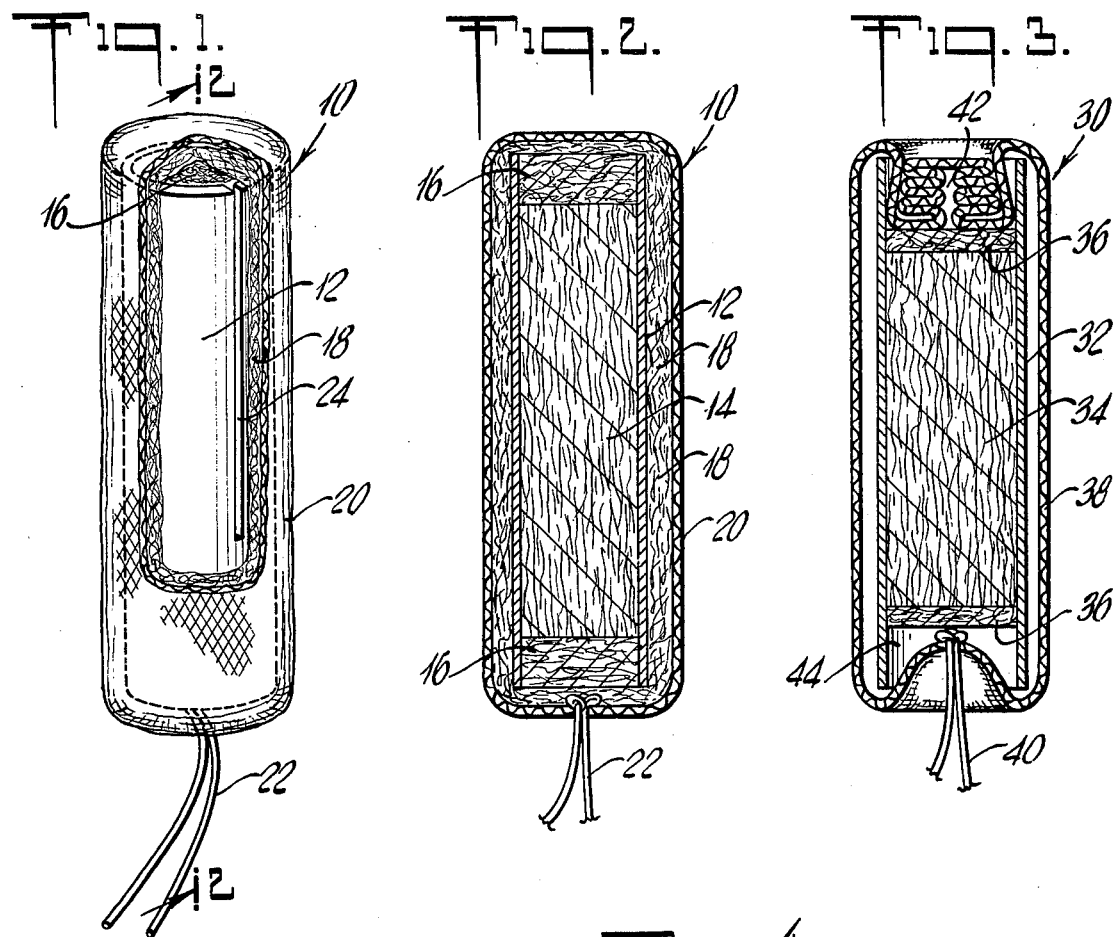
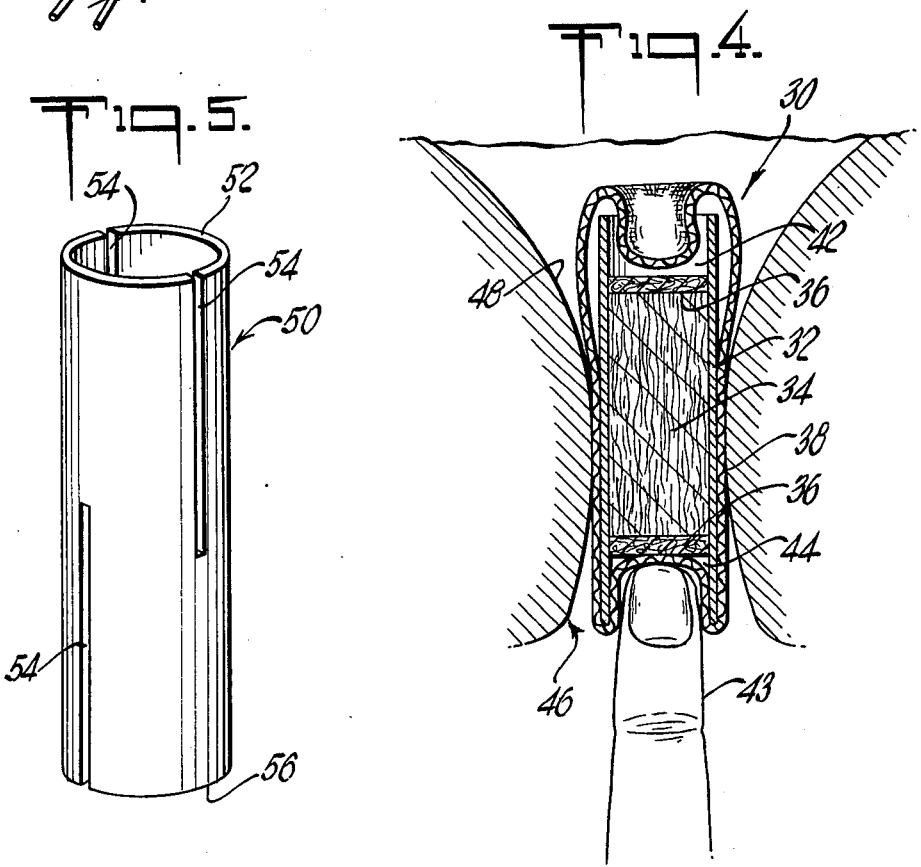

DIGITAL TAMPON

BACKGROUND OF THE INVENTION

This invention concerns catamenial tampons and more specifically, those catamenial tampons known as digital tampons which are designed to be inserted with the fingers and without the aid of such devices as plungers or stick-type applicators.

While many and varied configurations exist for the applicator-type tampon, heretofore the design and choice of materials for the construction of digital tampons have been limited by certain constraints. Since the digital type of tampon is designed to be inserted with only the assistance of the fingers, it is essential that the tampon be rigid enough to penetrate the introitus of the vagina in opposition to the muscular forces which tend to keep that orifice closed. Also, once past the introitus, the tampon must maintain a sufficient degree of rigidity to allow proper placement in the vaginal vault. Further, to avoid discomfort during insertion, the rigid tampon must be generally of a small diameter, approximately 1.2 to about 1.7 centimeters, and of a length no greater than about 5 centimeters. Needless to say, in addition to the constraints of rigidity and size, the tampon must be able to capture, i.e., absorb, entrap and/or retain, a sufficient quantity of menses. The tampon should also be capable of expanding when wet to minimize the possibility of menstrual fluid bypassing an emplaced tampon.

These constraints have until now greatly limited the choice of materials and hence, the functional properties of digital tampons. Such digital tampons as are presently on the market comprise a mass of cellulosic fibers such as cotton, rayon, wood pulp or the like, compressed into a generally cylindrical, rigid tampon shape. The cellulosic fibers will maintain their compressed shape when dry and when wet will expand somewhat to hold absorbed menses. The absorbency of such tampons is essentially prescribed by the size limitations set out above. A mass of cellulose fibers can be compressed to a limiting maximum density before a detrimental effect in absorbency is encountered. Because of this, the above size limitations, only a limited weight of fiber can be provided in a tampon and hence the maximum capacity of the tampon to absorb menses is prescribed. Further, since certain absorbent materials such as hydrophilic polyurethane foams and absorbent powders to do not readily compress into rigid bodies, to date the use of such materials in digital tampons has been precluded. Thus, while great progress has been made in the area of applicator-type tampons, the constraints of size and rigidity have greatly inhibited any enhancement of absorption capacity in digital tampons.

SUMMARY OF THE INVENTION

In accordance with this invention, a digital tampon is provided which meets the criteria of size and rigidity imposed upon prior digital tampon designs but which, by virtue of its unique construction, renders the absorption capacity of the tampon independent of the size and rigidity constraints.

Specifically, an improvement is provided in a catamenial tampon of the type comprising a generally cylindrical absorbent body adapted for digital insertion. The improvement comprises providing in such a tampon a separate and distinct rigidifying element extending longitudinally and disposed centrally with respect to the axis of the tampon. The element consists of a material having a dry resistance to compression sufficiently high enough to allow insertion and a wet resistance to compression, less than the dry resistance, and sufficiently low enough to allow the tampon to expand when wet and be comfortable in use. The provision of a rigidifying element with the above described properties allows for an almost unlimited choice of absorbent material for making up the rest of the tampon. This is in marked contrast with prior art tampons wherein the absorbent chosen had to be one capable of being compressed into a rigid tampon. Accordingly, materials such as the aforementioned hydrophilic polyurethane foam, which until now could only be used satisfactorily in applicator tampons, may now be used in a digital tampon.

The rigidifying element may take the shape of either a thin rod or a tube which could have a diameter as large as the tampon itself or alternatively, substantially smaller. When the element takes a rod-like form, the absorbent material making up the body of the tampon surrounds the rod and in particular, provides a protective cushion to prevent injury to the intravaginal surfaces during insertion. When the element takes the form of a tube, absorbent material may be provided both inside and/or outside the tube. In any event, it is important that the absorbent material be capable of expanding, in that once inserted, it is desirable for the tampon to expand in a manner which will tend to occlude the vagina to prevent menstrual fluid bypass.

Where absorbent material is positioned on the outside of the rigidifying element, clearly the expansion of this material when wet is totally unimpeded by the element. However, when the absorbent is contained within the rigidifying element as, for example, when contained within the tube shaped element, the element is provided with means for allowing the absorbent to expand. Such means for expansion may take any of several forms such as, for example, providing the tube-like rigidifying element with longitudinally extending slits which, when the rigidifying element is wet, allows the contained absorbent material to expand.

BRIEF DESCRIPTION OF THE DRAWINGS

The invention may be understood by reference to the following description taken in conjunction with the accompanying drawings in which:

FIG. 1 is a perspective view of an embodiment of the tampon of this invention shown with parts removed therefrom;

FIG. 2 is a cross-sectional view of the tampon of FIG. 1 taken along line 2—2;

FIG. 3 is another embodiment of the tampon of this invention shown in a cross-sectional view analogous to that of FIG. 2;

FIG. 4 is a cross-sectional view of the tampon shown in FIG. 3 while being inserted;

FIG. 5 is a perspective view of an embodiment of a rigidifying element for use in a tampon of this invention;

DETAILED DESCRIPTION OF THE INVENTION

Figure 6:
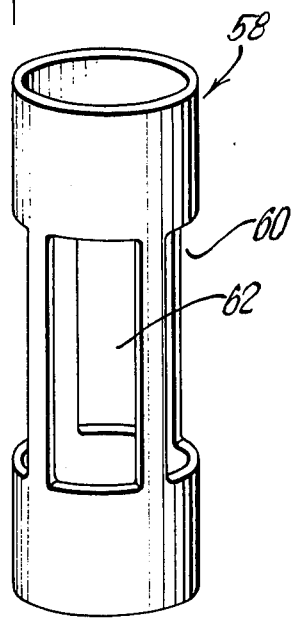
FIG. 6 is a perspective view of another embodiment of a rigidifying element for use in the tampon of this invention.

Referring now to FIGS. 1 and 2, shown there, in perspective and cross-sectional views, respectively, is a tampon 10 embodying the teachings of this invention. The tampon 10 comprises a generally cylindrically shaped absorbent body and is provided with a withdrawal string 22 for removing the tampon after use. In accordance with the invention, contained within the absorbent body is a rigidifying element 12 which, in this embodiment, is in the form of a relatively thin-walled tube having a diameter and a length less than the corresponding dimensions for the tampon. As will be described in greater detail below, the rigidifying element 12, when dry, has the property of imparting sufficient rigidity to the tampon structure to allow the tampon to be inserted and properly emplaced within the vaginal vault. Further, when wet, the element 12 will become soft so as to be comfortable and will be expandable so as to allow the tampon to act as an occlusive means to prevent menstrual fluid bypass. To further expandability, element 12 is provided with at least one slit 24.

The hollow tubelike element 12 is filled with a first absorbent 14 which may be any of the highly hydrophilic super-absorbent materials now know, such as for example, those derived from chemically modifying regeneration cellulose, natural cellulose or other polysaccharides such as starch, e.g., grafted cellulose copolymers and homopolymers such as cellulose having poly(acrylate) or poly(acrylate-ethyl acrylate) copolymer grafted to the cellulose backbone, etherified cellulose such as carboxy methyl-cellulose which is preferably rendered insoluble by cross-linking or by grafting polymer moieties thereto. In addition to such polysaccharides certain synthetically produced absorbent may be employed, e.g., polyurethane foam having been treated to be hydrophilic or polyacrylamide having chemically bonded thereto hydrophilic groups. Many other suitable absorbent materials as will occur to one skilled in the art may be employed.

The absorbent material may be in a self-sustaining form such as a single piece of hydrophilic foam, a compressed self-sustaining fibrous mass, or a wad of nonwoven fabric. Alternatively, the absorbent material may comprise loosely associated particulate matter, e.g., crumbs of hydrophilic foam or powderous absorbent material. In this case, the loosely associated absorbent material may be held in place within the rigidifying element 12 by retaining means 16 which can be in the form of disks of either absorbent material such as hydrophilic foam or wadded tissue or other nonwoven fabrics or simply a nonabsorbent retaining device such as a screen of polyethylene. The first absorbent 14 may also comprise a combination of any of the loosely associated and self-sustaining absorbents described herein.

Surrounding the filled rigidifying element 12 is a second absorbent 18 which may again comprise the self-sustaining and/or loosely associated material described above in connection with the first absorbent 14. Because this material is not as well contained as absorbent 14, it is preferred that absorbent 18 comprises either a self-sustaining material or a mixture of a self-sustaining material and particulate material. Of course, if the particulate material is of a substantial size, containment becomes less of a problem and such particulate matter is also useful as the second absorbent 18. An example of this latter case is in the use of relatively larger hydrophilic polyurethane foam crumbs.

As shown in FIGS. 1 and 2, the assembly of rigidifying element and first and second absorbent are all enclosed in a loosely fitting cover 20 which may be made of a fluid pervious nonwoven fabric or a fluid pervious woven material such as, for example, gauze. The cover 20 is provided to ensure that the components of the tampon 10 remain together during insertion and removal and additionally is used to contain the second absorbent when this absorbent comprises particulate matter. Further, the cover may be chosen to have lesser frictional resistance than the absorbent material and will, therefore, facilitate insertion of the tampon.

Because the absorbent material in the tampon is designed to expand when wet and advantageously occlude the vagina, the cover is only loosely fitted to the tampon assembly to allow for such expansion.

Illustrated in FIG. 3 is another tampon 30 embodying this invention wherein a tubular rigidifying element 32 is provided containing a first absorbent 34 optionally held in place by retaining disks 36. The rigidifying element, the first absorbent and the retaining disks all are meant to serve the same function as that described in connection with FIGS. 1 and 2 and, hence, may all be comprised of the same or similar materials. Again, a cover 38 is provided to hold the assembly together and to ease insertion. Also, a withdrawal string 40 is provided for removing the tampon 30.

In contrast to the embodiment shown in FIGS. 1 and 2, no second absorbent has been provided outside the rigidifying element 32. In fact, the tubular rigidifying element 32 is not completely filled with absorbent 34 and disks 36 but, instead a first void space 42 has been provided at the leading end (with respect to insertion) of the tampon and a second void space 44 has been provided at the lagging end of the tampon. The cover 38 which, as was the case in the foregoing embodiment, is loosely fitted to allow for tampon expansion, is tucked into first void space 42 prior to use.

Referring now to FIG. 4, shown there is the tampon 30 being inserted. The finger of the user 43 fits into the second void space 44 and guides the tampon into place in a controlled manner. As the tampon 30 is inserted through the introitus 46 of the vagina, the friction of the cover 38, acting against the vaginal mucosa 48, untucks the portion of the cover tucked into the first void space 42 while at the same time forces this cover material around the finger guiding the tampon. This is advantageous in that, in addition to untucking the cover so that the tampon may expand, the material surrounds and protects the guiding finger during insertion.

As described in connection with FIGS. 1-3, the rigidifying elements 12 and 32 must have the properties of being rigid when dry, yet soft and flexible when wet and must allow the tampon to expand in use. A great many materials and configurations for the rigidifying element can be used to obtain these properties. In general, the rigidifying element should exhibit a column strength as determined by compression testing, of at least 1.5 kg. in order to have sufficient rigidity to be properly inserted. The column strength, as the term is used herein, is determined by placing the rigidifying element between the jaws of a Chatillon Universal Tester, the jaws being set to move at a rate of 5 inches per minute. The rigidifying element is so placed as to have its axis parallel to the direction of jaw movement and the column strength is determined by the value of the stress just before the rigidifying element collapses, i.e., the maximum value for stress before the stress suddenly drops. Further, from the point of view of user comfort both while wearing the tampon and during removal, the column strength of the rigidifying element when wetted with menstrual fluid should be reduced to a value less than about 0.5 kg.

It will be appreciated that column strength, as defined herein, is a function of both the materials of construction for the rigidifying element as well as the specific configuration, i.e., the wall thickness, diameter and the like are all factors in determining column strength. Thus, for example, the rigidifying element 12 shown in the embodiment illustrated in FIGS. 1 and 2 will have a lesser column strength, all other factors being equal, than the element 32 of FIG. 3 in that the diameter of element 12 is less than the outside diameter of the tampon 10, whereas the diameter of element 32 is about equal to the diameter of the tampon 30, assuming both tampons are of equal diameter.

A wide variety of materials may be satisfactorily employed as materials of construction for the rigidifying element of this invention and will exhibit the requisite change in column strength when going from a dry to a wet state. One readily available and completely satisfactory material is the fibrous boards, commonly referred to as "cardboard". This term is applied to boards, 0.006 of an inch or more in thickness, which are made primarily with stiffness as the paramount characteristic. The paper industry in general uses the term "board" to describe this material, usually prefacing the term "board" with modifiers such as Blanks, Bristols, Chip, Paper, Paper-Starch, Railroad, Thick China, Tough Check, Translucents, etc. which indicate its character or use. Each of these boards may be used provided that, in accordance with the teachings of this invention, the board is chosen in connection with the other configuration parameters to give the desired column strength when wet and dry. In some cases it may be necessary to omit the special finishes normally applied to the board which could interfere with a reduction in column strength when saturated with fluid.

In addition to cardboard, many natural and synthetic materials will occur to one skilled in the art as being useful for the construction of the rigidifying element in that they have the herein described requisite properties. A wide variety of polymers exist which can be molded into the shape of the rigidifying element and will exhibit the aforementioned wet and dry column strengths. For example, certain hydrophilic polymers such as the poly(hydroxyethyl acrylates) or hydroxypropyl cellulose are useful. Others include grafted cellulose board, starch-based materials, gelatine. Still further, materials which normally do not have the requisite column strength when dry such as fabrics, both woven or nonwoven, e.g., gauze, paper, tissue, may be treated with stiffeners such as starch so as to be rigid when dry yet will lose such rigidity when wet.

Figure 7:
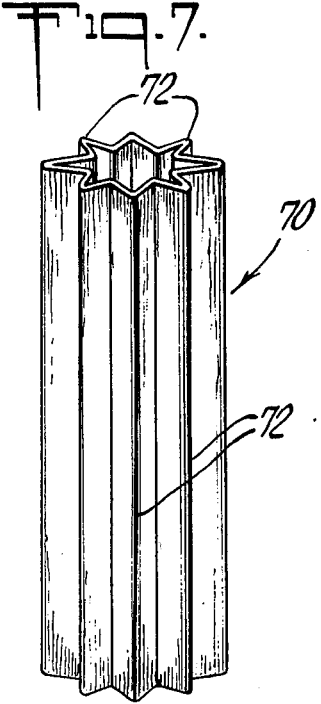
FIG. 7 is a perspective view of still another embodiment of a rigidifying element for use in the tampon of this invention.

In addition to having the property of being soft and nonrigid when wet, it is important that the tubular, absorbent-filled, rigidifying element described in connection with FIGS. 1-4 allow the absorbent to expand when wet and enable the tampon to act as an occlusion means in the vagina. FIGS. 5-7 illustrate several designs for a rigidifying element which will allow for such expansion. These elements may all be constructed from the materials described above. Illustrated in FIG. 5 is a tubular thinwalled cylindrical element 50 which is provided with one or more longitudinally extending slits 54 cut through the cylinder wall. Each of the slits may extend from the first cylinder end 52 to midway toward the second cylinder end 56 or even completely to the end 56, provided the material of construction of element 50 is sufficiently strong enough when dry to maintain its general shape when so slit. It has been found, for example, that elements 2 inches in length by about ½ inch in diameter and constructed of cardboard having a thickness of 0.020 inches will have dry column strengths in excess of 5.0 kilograms when provided with a single slit extending from one cylinder end to the other. Alternatively, such elements will have essentially the same dry column strength when provided with four slits equally radially spaced and extending longitudinally from alternate cylinder ends to about 1¾ inches toward the other cylinder end. When the tampon is wet with menstrual fluid and the element loses its rigidity, the wet expanding absorbent material contained within the element easily widens the slits to the extent that the element affords no significant impediment to expansion.

It will be apparent from the foregoing that while slits are illustrated in FIG. 5 as being formed by a removal of material from the walls of the cylinder, a simple cut or perforation of the wall will also be satisfactory.

Illustrated in FIG. 6 is rigidifying element 58 provided with another means for allowing expansion of a contained absorbent. Again, the element 58 comprises a cylindrical, thinwalled tube, but in this case, the tube is provided with a plurality of cut-out areas 60 and 62, for example, which can represent as much as 30% of the total cylinder wall area. Absorbent material contained within the element 58 may therefore expand through these cut-out areas and in fact, may, by virtue of the force exerted during expansion, sever the ribs separating adjacent cut-out areas, thus allowing for still further expansion.

Illustrated in FIG. 7 is still another rigidifying element 70 which may be used in the invention. In this case, the means for allowing expansion comprise providing radially spaced longitudinal folds 72 around the walls of the cylindrical element 70 which are alternatively folded toward and away from the axis of the cylinder so as to form an accordion pleated surface. When pressure is exerted upon the folded pleats, such as is the case when the confined absorbent expands upon wetting, the pleats open to increase the diameter of the element 70.

Figure 8:
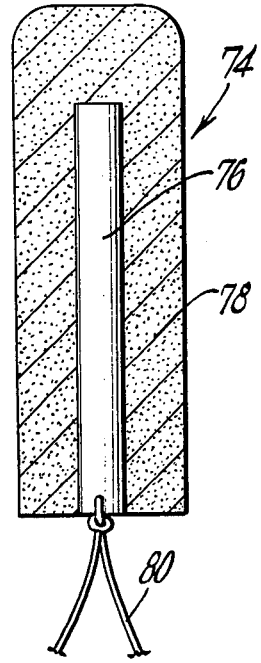
FIG. 8 is another embodiment of the tampon of this invention shown in a cross-sectional view analogous to that of FIG. 2.

FIG. 8 illustrates another embodiment of the invention. Shown there is a tampon 74 wherein a rigidifying element 76 is provided which should have the same wet and dry column strengths described in connection with the prior embodiments and hence, may be constructed of the same or similar materials. In constrast, however, to the hollow cylindrical elements of the prior embodiments, element 76 is in the form of a centrally located solid rod, extending longitudinally with respect to the axis of the tampon. Element 76 advantageously requires no special means for allowing absorbent expansion as the rod creates no impediment to expansion. It is important, however, that the rod be cushioned so as to protect the user. Generally, this is easily accomplished by use of the absorbent itself. For example, in FIG. 8, the element 76 is completely surrounded by a first absorbent 78 which may be a solid piece of molded polyurethane foam. A withdrawal string 80 is attached to the end of the tampon 74 and is preferably anchored to the element 76.

Figure 9:
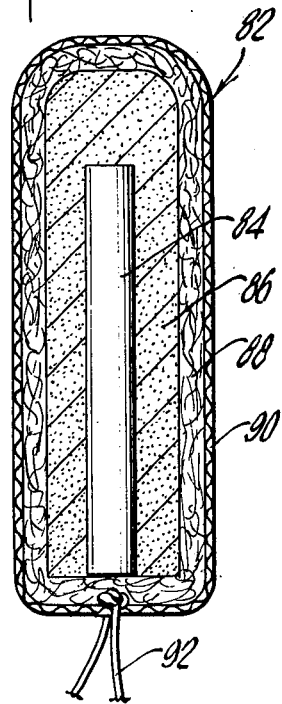
FIG. 9 is still another embodiment of the tampon of this invention shown in a cross-sectional view analogous to that of FIG. 2.

Illustrated in FIG. 9 is an alternative to the embodiment shown in FIG. 8. Tampon 82 comprises a centrally located, longitudinally extending rigidifying element 84 which again possesses the wet and dry properties described herein and again may be constructed from those materials of construction set out with respect to prior described embodiments. In this embodiment, the rigidifying element 84 is again surrounded by a cushioning first absorbent 86. The absorbent 86 is in turn surrounded by a second absorbent 88 which may be, for example, either a self-sustaining absorbent or a particulate absorbent. In the latter case, it is most desirable to enclose the tampon assembly in a pervious cover 90. The usual withdrawal string 92 is provided, in this case attached to the cover by means such as adhesive, for example.

EXAMPLE 1

A series of tampons are prepared having the general configuration of those illustrated in FIGS. 1 and 2 of the drawings and utilizing various materials for the first and second absorbents positioned as described above in connection with these figures. Table I is a tabulation of details of construction and absorbent properties of those tampons. The indication of "GC" as an absorbent is meant to denote an absorbent of the kind described in U.S. Pat. No. 3,889,678 issued on June 17, 1975 to P. K. Chatterjee and R. F. Schwenker Jr. and specifically cellulose — Sodium Poly(acrylate - ethylacrylate) copolymers. "PU" denotes a flexible, hydrophilic polyurethane foam obtained from Scott Paper Company and sold by them under the trademark Acquell. "RAY/COT" denotes a mixture consisting of 30% by weight cotton fibers having an average staple length of ⅜ inches (0.94 cm.) and 70% by weight of 3.0 denier rayon having an average staple length of 1⅛ inches (2.82 cm). As is noted in Table I, in some instances, retaining disks are provided made of various materials. Further, in some instances, the second absorbent is dispensed with and similarly, the nonwoven cover is also dispensed with.

In all cases where a cover is used, the cover consists of a nonwoven, fluid impervious fabric comprising fibers of spun — bonded polyester. Such fabric is sold by E. I. DuPont de Nemours under the trademark Reemay. For each of the samples, the rigidifying element consists of a slit, thin-walled cardboard tube having an overall length of 5 cm. and outside diameter of 1.3 cm. and a wall thickness of 0.08 cm. The cardboard has a density of 0.35 gm./cm³. All slit configurations are longitudinal and extend from one end to 0.635 cm. of the other end. Single and quadruple slits and multi-perforated slits are used.

Each of the tampons exhibits a dry column strength in excess of 5 kg.

Each of the tampons is tested for their ability to absorb a 1% by weight aqueous sodium chloride solution under simulated in-use conditions. The test comprises flooding one end of a tampon in the test solution while maintaining the sides of the tampon under a confining pressure (for this specific test, 0.3 pounds per square inch gauge) which is maintained by enveloping the tampon in a pneumatically pressurized rubber sleeve. The tampon is maintained flooded until fluid appears on the non-flooded end of the tampon at which time free solution is drained from the system while still maintaining the confining pressure. The pressure is then released and the weight of solution absorbed by the tampon is reported in Table I in terms of the specific absorbency of the tampon, i.e., the total volume of fluid held by the tampon at the completion of the test divided by the dry weight of the tampon.

TABLE I

| Sample | First Absorbent | Second Absorbent | Details of Construction | Specific Absorbency (ml/gm) |
|---|---|---|---|---|
| 1 | GC/0.9 | — | Tissue retaining disks and no cover | 8.26 |
| 2 | GC/1.17 | — | No retaining disks, Reemay* nonwoven cover | 7.71 |
| 3 | GC/0.46 | — | PU (0.49 gm.) retaining disks, no cover | 7.45 |
| 4 | PU/0.81 | PU/0.52 | No retaining disks, no cover | 7.05 |
| 5 | GC/0.90 | — | Cellulose sponge retaining disks, Reemay* nonwoven cover | 6.87 |
| 6 | PU/0.9 | PU/0.66 | No retaining disks, no cover | 6.33 |
| 7 | PU/1.01 | PU/0.72 | No retaining disks, no cover | 6.08 |
| 8 | GC/1.08 | — | PU (0.37 gm.) retaining disks, Reemay* nonwoven cover | 6.06 |

*Trademark

For comparative purposes, a conventional compressed rayon fiber tampon now on the market and sold by the Personal Products Company under the trademark Carefree is tested for specific absorbency by the method described above and results in specific absorbency of 4.2 ml/gm. Considering this, together with the data in Table I, it can be seen that, depending upon such factors as details of construction and type and weight of absorbents employed, tampons constructed in accordance with the teachings of this invention and specifically, in accordance with the embodiment shown in FIGS. 1 and 2, may have varying specific absorbency and may, in most cases, be designed to have substantially higher specific absorbencies than conventional tampons.

EXAMPLE 2

A second series of tampons are prepared having the general configuration of that illustrated in FIG. 3 wherein the second absorbent is entirely dispensed with. In all other respects, this series of tampons utilizes the same construction parameters described in connection with the prior example. Table II is a tabulation of the details of construction and absorbent properties of these tampons. The specific absorbency is determined using the test described above.

TABLE II

| Sample | First Absorbent Type Wt. (gm.) | Details of Construction | Specific Absorbency (ml/gm) |
|---|---|---|---|
| 9 | GC/0.98 | Tissue retaining disks, Reemay* nonwoven cover. | 5.99 |
| 10 | GC/1.72 | No retaining disks, Reemay* nonwoven cover. | 4.53 |
| 11 | GC/1.47 | Absorbent retained in nonwoven bag within rigidifying elements, Reemay* nonwoven cover. | 4.20 |

*Trademark

As the above data indicates, this embodiment of the invention again produced a moderately wide range of specific absorbencies, all of which were at least equal to a conventional tampon.

EXAMPLE 3

Samples of the tampon illustrated in FIGS. 8 and 9 are prepared. The rigidifying element consists of a solid cylinder, 3.8 cm. long and 0.3 cm. in diameter. The rod is composed of compressed cellulose fibers (cardboard). The rigidifying element is cushioned and surrounded by first and second absorbents as set out in Table III, wherein the materials of construction are denoted in the same manner as in connection with Examples 1 and 2. This series of tampons are again tested for absorbency as in Example 1 with the results being reported in Table III.

TABLE III

| Sample | Absorbent Type/Wt.(gm.) | | Details of Construction | Specific Absorbency |
| --- | --- | --- | --- | --- |
| | First Absorbent | Second Absorbent | | |
| 12 | Cellulose Sponge/1.00 | PU/0.48 | Keybak* non-woven cover | 6.15 |
| 13 | RAY/COT/1.16 | PU/0.31 | Reemay* non-woven cover | 4.75 |
| 14 | Ra/COT/1.22 | PU/0.61 | Reemay* non-woven cover | 4.19 |

*Trademark

As the above data show, a wide range of specific absorbency is obtained, all being at least equal to that of a conventional tampon. When dry, the tampons all exhibit sufficient rigidity for insertion and when wet, the rigidity of all tampons is reduced to be comfortable when worn and removed.

What is claimed is:

1. In a catamenial tampon of the type comprising a generally cylindrical absorbent body and adapted for digital insertion, the improvement which comprises: providing therein an at least partially absorbent rigidifying element extending longitudinally and disposed centrally with respect to the axis of said tampon; said element consisting of a material having a dry resistance to compression sufficient to allow insertion and a wet resistance to compression less than the dry resistance and sufficiently low enough to allow said tampon to expand and be comfortable in use.

2. The catamenial tampon of claim 1 wherein said rigidifying element has a dry column strength of at least 1.5 kg.

3. The catamenial tampon of claim 2 wherein said rigidifying element has a wet column strength of less than 0.5 kg.

4. The catamenial tampon of claim 1 wherein said rigidifying element is a hollow thin-walled tube.

5. The catamenial tampon of claim 4 wherein said hollow tube is at least partially sealed with a hydrophilic absorbent.

6. The catamenial tampon of claim 5 wherein said hydrophilic absorbent expands upon being wetted and said hollow tube is provided with means for allowing said expansion.

7. The catamenial tampon of claim 6 wherein said means for allowing expansion comprises at least one longitudinally extending slit cut through the wall of said hollow tube.

8. The catamenial tampon of claim 1 wherein said rigidifying element is cardboard.

* * * * *